United States Patent
Fan et al.

(10) Patent No.: US 10,549,265 B2
(45) Date of Patent: Feb. 4, 2020

(54) DIETHYL OXALATE CATALYSTS

(71) Applicant: University of Wyoming, Laramie, WY (US)

(72) Inventors: Maohong Fan, Ames, IA (US); Erlei Jin, Laramie, WY (US)

(73) Assignee: University of Wyoming, Laramie, WY (US)

(*) Notice: Subject to any disclaimer, the term of this patent is extended or adjusted under 35 U.S.C. 154(b) by 0 days.

(21) Appl. No.: 14/749,222

(22) Filed: Jun. 24, 2015

(65) Prior Publication Data

US 2016/0023189 A1 Jan. 28, 2016

Related U.S. Application Data

(60) Provisional application No. 62/018,471, filed on Jun. 27, 2014.

(51) Int. Cl.
*B01J 23/63* (2006.01)
*C07C 67/36* (2006.01)
*B01J 35/02* (2006.01)
*B01J 35/10* (2006.01)

(52) U.S. Cl.
CPC ............ *B01J 23/63* (2013.01); *B01J 35/023* (2013.01); *C07C 67/36* (2013.01); *B01J 35/1009* (2013.01); *B01J 35/1014* (2013.01)

(58) Field of Classification Search
None
See application file for complete search history.

(56) References Cited

FOREIGN PATENT DOCUMENTS

CN 101993368 * 3/2011

OTHER PUBLICATIONS

Machine translation fro CN 101993368.*
NIOSH Pocket Guide to Chemical Hazard.*
Zhao et al. Applied Catalysis A: General, 284 (2005) 253-257.*
Chemical Technology PEP Review 2012, p. 1-2.*
Qingling et al., "Recent Advances in Coal to Chemicals Technology Developed by SINOPEC", "Journal of Catalysis", 2013, pp. 217-224, vol. 34, Publisher: SINOPEC.
Yamamoto et al, "Catalysis and characterization of Pd/NaY for dimethyl carbonate synthesis from methyl nitrite and CO", "J Chemical Society", Jan. 1997, pp. 3721-3727, vol. 93, No. 20.
Zhuo et al., "Catalytic Decomposition of Ethyl Nitrite over Supported Palladium Catalyst", "Chinese Journal of Catalysis", Jul. 2003, pp. 509-512, vol. 23, No. 7.
Gao et al., "CFD modeling of gas flow in porous medium and catalytic coupling reaction from carbon monoxide to diethyl oxalate in fixed-bed reactors", "Chemical Engineering Science", 2011, pp. 6028-6038, vol. 66, Publisher: Elsevier.
Zhao et al, "Characterization of PdCeO2/a-alumina catalyst for", "Applied Catalysis", 2005, pp. 253-257, vol. 284, Publisher: Elsevier.
Li et al., "Clean Coal COnversion Processes—Progress and Challenges", "Energy Enviommental Science", 2008, pp. 248-267, vol. 1, Publisher: Royal Society of Chemistry.
Zhenghong et al., "Combined XPS and in situ DRIRS study of mechanism of PdFe/-Al2O3 catalyzed CO coupling reaction to diethyl oxalate", "Journal of Molecular Catalysis: A Chemical", 2005, pp. 143-149, vol. 235, Publisher: Elsevier.
Gao et al., "A PdFe/a-Al2O3/cordieritemonolithiccatalystforCOcouplingtooxalate", "Chemical Engineering Science", 2011, pp. 3513-3522, vol. 66, Publisher: Elsevier.
Jiang et al., "Design of a two-stage fluidized bed reactor for preparation of diethyl oxalate from carbon monoxide", "Chemical Engineering Research and Design", 2012, pp. 915-925, vol. 90, Publisher: Elsevier.
Bae et al., "Economic Evaluations of Direct, Indirect and Hybrid Coal Liquefaction", "Korean J. Chem.Eng.", 2012, pp. 868-875, vol. 29, No. 7.
Li et al., "Effect of Hydrogen on Catalytic Coupling Reaction of Carbon Monoxide to Diethyl Oxalate", 2001, pp. 135-142, vol. 73, No. 1, Publisher: Akadmiai Kiad, Budapest, Published in: Budapest.
Lin et al., "Effects of Precursors on Preparation of Pd/r-alumina Catalyst for Synthesis of Dimethyl Oxalate", "Ind. Eng. Chem Res.", 2007, pp. 7950-7954, vol. 46, Publisher American Chemical Society.
Zhang et al., "The effects of cornstalk addition on the product distribution and yields", "Applied Energy", 2014, pp. 1-6, vol. 130, Publisher: Elsevier.
"Ethylene Glycol Production form Coal-Based Synthesis Gas", Oct. 2012, pp. 12, Publisher: IHS Inc.
Dry, Mark E., "The Fischer-Tropsch Process: 1950-2000", "Catalysis Today", 2002, pp. 227-241, vol. 71, Publisher: Elsevier.
Othmer et al., "Glycol Production—Hydration of Ethylene Oxide", "Insustrial and Engineering Chemistry", Sep. 1958, pp. 1235-1244, vol. 50, No. 9, Publisher: Polytechnic Instuitue, Published in: Brooklyn NY.
Xu et al., "High-Performance and Long-Lived Pd Nanocatalyst Directed by", 2012, pp. 118-122, vol. 3, Publisher: American Chemical Society.
Jin, Erlei et al., "Indirect Coal to Liquid Technologies", "Applied Catalysts", 2014, pp. 158-174, vol. 476, Publisher: Elsevier.
Quin et al., "Influence of Oxygen on Activity of PD-FE A12O3 Catalyst for CO Coupling Reaction to Diethyl Oxalate", "Chinese Journal of Catalysis", 2003, pp. 289-293, vol. 24, Publisher: University of Wyoming Libraries.
Meng et al., "Kinetic study of carbon monoxide coupling reaction over supported palladium catalyst", "Chemical Engineering and Processing", 2004, pp. 785-790, vol. 4, Publisher: Elsevier.
Meng et al., "Kinetics of the catalytic coupling reaction of carbon monoxide to diethyl oxalate over Pd-Fe/-Al2O3 catalyst", "Science Direct", 2003, pp. 283-288, vol. 201, Publisher Elsevier.

(Continued)

*Primary Examiner* — Ana Z Muresan
(74) *Attorney, Agent, or Firm* — Davis, Brown, Koehn, Shors & Roberts, P.C.; Matthew W. Coryell

(57) ABSTRACT

A highly effective catalyst for the preparation of diethyl oxalate using carbon monoxide using Pd/α-Al$_2$O$_3$ and CeO$_2$ as a promoter. High conversion rates with greatly extended catalyst life is achieved with the CeO$_2$-enhanced Pd catalysts. The catalysts can be used for the production of high-value diethyl oxalate, and eventually ethylene glycol, from coal-derived syngas.

13 Claims, 6 Drawing Sheets

(56) References Cited

OTHER PUBLICATIONS

Xu et al., "Kinetics of the Hydrogenation of Diethyl Oxalate to Ethylene Glycol", "Industrial Engineering Chem.", 1995, pp. 2371-2378, vol. 34, Publisher: American Chemical Society.

Sadeghi et al., "Bimetallic Ag/Co Synthesized at Liquid/Liquid Interface with Controllable Core/Shell Structures", Nov. 18, 2015, pp. 177-184, Publisher: Univeristy of Wyoming Libraries.

Jenks et al, "Photoelectron spectra of an Al70Pd21Mn9 quasicrystal and the cubic alloy Al60Pd25Mn15", "Physical Review B", Sep. 1996, vol. 54, No. 9, Publisher: The American Physical Society.

Naik et al., "Production of first and second generation biofuels: A comprehensive review", "Renewable and Sustainable Energy Reviews", 2010, pp. 578-597, vol. 14, Publisher: Elsevier.

Heyuan et al., "Progress in synthesis of ethylene glycol through C1 chemical", "Chinese Journal of Catalysis", 2013, pp. 1035-1050, vol. 34, Publisher: Elsevier.

Gao et al., "Study on Ammonia Poisoning of PD System Catalyst for CO Coupling Reaction to Diethyl Oxalate", "Chinese Journal of Catalysis", 2002, pp. 95-98, vol. 23, Publisher: University of Wyoming Libraries.

Zhenghong, "Surface Structure of PD-FE/a-Al2O3 catalyst for CO coupling to Diethyl Oxalate", Mar. 2004, pp. 205-209, vol. 25, No. 3, Publisher Chinese Journal of Catalysis.

Zhao et al., "Synthesis of Dimethyl Oxalate form CO and CH3ONO on Carbon Nanofiber Supported Palladium catalysts", "Ind. Eng. Chem. Res.", May 28, 2004, pp. 4595-4601, vol. 43, Publisher: American Chemical Society.

Kumar et al., "Thermochemical Biomass Gasification: A Review of the Current Status of the Technology", "Energies", 2009, pp. 556-581, vol. 2, Publisher: MDPI.

Kotowski et al., "Wytwarzanie Glikolu Etylenowego Metoda Hydroformylowania Formaldehydu", "Przemysl Chemiczny", 1989, pp. 73-76, vol. 68.

Moddeman et al., "XPS Surface and Bulk Studies of Heat Treated Palladium in the Presence of Hydrogen at 150C", "Surface and Interface Analysis", 1988, pp. 317-326, vol. 11, Publisher: John Wiley and Sons Ltd.

Tressaud, "X-Ray Photoelectron Spectroscopy of Palladium Fluorides", "Zeitschrift Fur Anorganische Und Allgemeine Chemie", 1986, pp. 291-299, vol. 541.

* cited by examiner

DIETHYL OXALATE CATALYSTS

CLAIM OF PRIORITY

This application claims priority to U.S. Patent Application Ser. No. 62/018,471, filed Jun. 27, 2014, and which is incorporated herein in its entirety by this reference.

BACKGROUND OF THE INVENTION

The present invention relates generally to catalysts of the production of diethyl oxalate from carbon dioxide and, more specifically, to highly effective palladium catalysts promoted with cerium.

Ethylene glycol (EG) is a crucial raw material with a global demand of around 25 million tons each year, which is mostly produced through traditional petrochemical technology.[1, 2] However, the cost of this production is relatively high due to the continuous increasing price of natural gas and crude oil, and dwindling sources of petroleum. Furthermore, strong acids or alkalis such as sulfuric acid or sodium hydroxide have to be used through the traditional method, which causes severe corrosion to the equipment and environmental problems.[3] Therefore, a green route which is independent of petroleum while achieves high yield of EG is in demand and of great significance.

Coal is the most abundant energy reserve in the world that some people like because of their needs while others hate due to the various emissions resulting from its combustion. [4] To reduce $CO_2$ emission and produce high-value fuels and chemicals from coal, coal gasification and liquefaction technologies have attracted increasing interest during the past few decades.[5-8] Coal to ethylene glycol, as a potentially green and economic coal liquefaction technology, has been attracting extensive attention in both academic and business circles in the past decades. [9-12] Although it is challenging to achieve high industrial production levels, due primarily to achieving good performance of the catalysts, this technology has been scaled-up to industrial levels of production in China and Europe. Until now, China leads the word in this area and successfully built the world's first annual 200 thousand tons coal to ethylene glycol production plant in 2009.[13]

Syngas to ethylene glycol contains several steps and the step of CO oxidative coupling to di-alkyl oxalate is the critical step since di-alkyl oxalate is required for hydrogenation to EG.

$$2CO+2RONO \rightarrow (COOR)_2+2NO \quad (1)$$

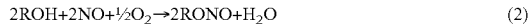

$$2ROH+2NO+\tfrac{1}{2}O_2 \rightarrow 2RONO+H_2O \quad (2)$$

Two main chemical reactions are involved in the CO oxidative coupling step, coupling reaction and regeneration reaction, which are shown in Eq. (1) and (2) separately. The reaction in Eq. (1) occurs on supported metal catalysts, where R could be methyl, ethyl or butyl groups. The regeneration reaction shown in Eq. (2) doesn't need any catalyst. Esterification between oxalic acid and alcohol has been employed as a traditional way of synthesizing oxalic ester. However, this method has several problems, such as severe pollution, high energy consumption and high upfront costs. Therefore, oxidative coupling reaction of CO and alkyl nitrite, forming oxalic ester, has been extensively researched in the past decades. [3, 14-20]

Various supported palladium catalysts for gas-phase synthesis of dimethyl oxalate (DMO) or diethyl oxalate (DEO) have been investigated, and the results have demonstrated that higher conversion and selectivity are realized on Pd/α-$Al_2O_3$ compared to Pd on active carbon or γ-$Al_2O_3$.[21, 22] However, the relatively high Pd loading (around 2 wt %) is always an issue for industrial application of CO oxidative coupling to OMO, which will greatly increase the cost of production. Therefore, the design of low Pd loaded catalysts with high performance is important to industry. A Pd/α-$Al_2O_3$ nanocatalyst with ultra-low Pd loading that exhibits high activity and stability for CO oxidative coupling to DMO was developed recently. [23] This catalyst was prepared by a $Cu^{2+}$ assisted in situ reduction method at room temperature, which significantly increased the dispersion and the specific area of active component Pd, and also decreased the ensemble size of Pd nanoparticles dispersed over the Pd/α-$Al_2O_3$. The average size of Pd nanoparticles is 2.7 nm, and the Pd loading could be as low as 0.13 wt %. To further enhance the activity and stability of Pd/α-$Al_2O_3$, several metals such as Fe, [24, 25] Ni and Ce were reported as promoters to enhance the dispersion of Pd on the support or decrease the Pd particles size.[24-27] $CeO_2$ was reported as a promoter and in spite of the reaction was evaluated only within 100 min, Pd—$CeO_2$/α-$Al_2O_3$ catalyst showed around 20% higher catalytic activity compared to Pd/α-$Al_2O_3$ catalyst (without $CeO_2$) for the synthesis of DMO from CO and methyl nitrite. [28]

Although methyl nitrite has been maturely used, especially in China, for the industrial synthesis of DMO, it is controlled in the US due to its highly flammable, highly explosive and toxic properties. Ethyl nitrite, however, is another safe and non-explosive alkyl nitrite that also can be used for CO oxidative coupling reaction.[18, 20, 29-31] Therefore, to find a good catalyst with low Pd loading and high catalytic activity for CO oxidative coupling to DEO is of great significance in the US. Herein, we report a Pd—$CeO_2$/α-$Al_2O_3$ nanocatalyst with 0.8% Pd (wt %) loading and 0.2 wt % $CeO_2$ as a catalyst for CO oxidative coupling to DEO. We present the preparation and characterization of two catalysts with and without $CeO_2$ as a promoter. The comparison of catalytic activities between the two catalysts is discussed and the interaction among Pd, ceria and the support leading to the activity differences is also presented.

SUMMARY OF THE INVENTION

The present invention involves highly effective catalysts for preparation of diethyl oxalate (DEO) using CO from coal-derived syngas. Pd/α-$Al_2O_3$ nanocatalysts were synthesized and $CeO_2$ was used as a promoter. The nanocatalysts were characterized with various techniques including X-ray diffraction (XRD), X-ray photoelectron spectroscopy (XPS), transmission electronic microscopy (TEM), scanning transmission electronic microscopy (STEM) and scanning electronic microscopy (SEM), and evaluated with a packed bed reactor. The obtained best catalyst contains of 0.9 wt % Pd and 0.2 wt % $CeO_2$ with its size and specific surface area being 13 nm and 5.6 $m^2/g$, respectively. The catalyst promoted with $CeO_2$ achieved as high as 62% CO conversion, more than 50% increase compared to that without $CeO_2$, while the same DEO selectivity (93%). Moreover, the high CO conversion maintained as long as 72 h, about 42 times longer than that reported in literature. Therefore, a $CeO_2$ promoted Pd/α-$Al_2O_3$ is a highly active and stable nanocatalyst for production of high-value DEO and eventually EG from coal-derived syngas.

DETAILED DESCRIPTION OF THE PREFERRED EMBODIMENTS

Figure 1:
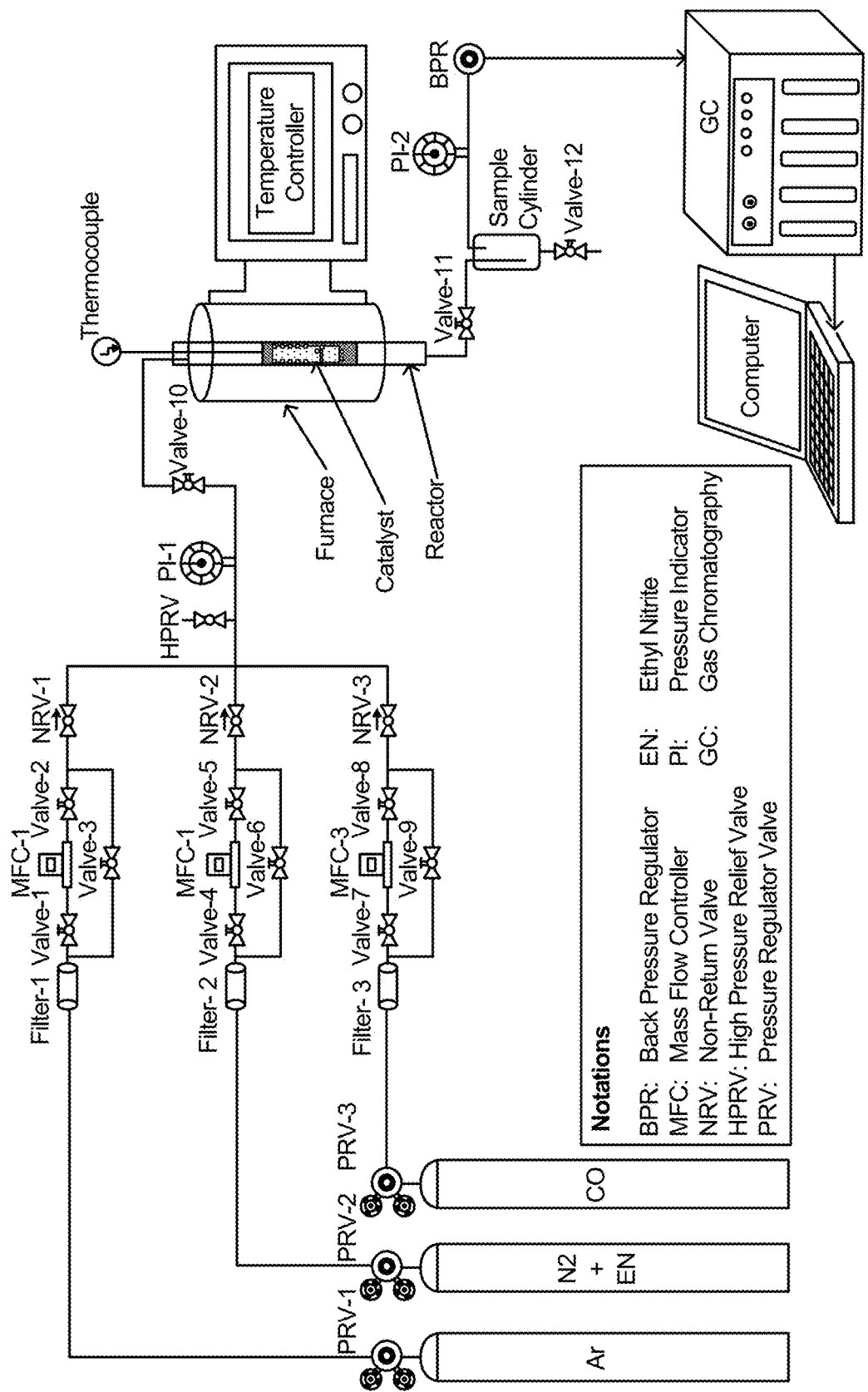
FIG. 1 is a schematic diagram of the apparatus used in the conversion of ethylene nitrite to diethyl oxalate.

As used herein, a "promoter" or "enhancer" is a chemical that is added to a catalyst to improve the performance of the catalyst in catalyzing a chemical reaction.

The Pd catalysts promoted by CeO$_2$ of the present invention had optimal performance characteristics when used at a Pd loading of between 0.1 wt % and 1.2 wt %, more preferably between 0.4 wt % and 1.4 wt %, and even more preferably between 0.7 wt % and 1.0 wt %.

The Pd catalysts promoted by CeO$_2$ of the present invention had optimal performance characteristics when used at a CeO$_2$ loading of between 0.02 wt % and 1 wt %, more preferably between 0.07 wt % and 0.6 wt %, and even more preferably between 0.15 wt % and 0.25 wt %.

The Pd catalysts promoted by CeO$_2$ of the present invention had optimal performance characteristics when the Pd particles had an average size of between 2 nm and 80 nm, more preferably between 5 nm and 40 nm, and even more preferably between 9 nm and 17 nm.

The Pd catalysts promoted by CeO$_2$ of the present invention had optimal performance characteristics when the Pd particles had an average surface area of between 1 m$^2$/g and 20 m$^2$/g, more preferably between 2 m$^2$/g and 12 m$^2$/g, and even more preferably between 3 m$^2$/g and 8 m$^2$/g.

The Pd catalysts promoted by CeO$_2$ of the present invention maintained a high conversion rate for a time between 2 and 100 times longer, more preferably between 10 and 70 times longer, and even more preferably between 30 and 55 times longer, than Pd catalysts that had not been promoted with CeO$_2$.

Where ranges are used in this disclosure, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3, 6.3, 0.815 and so forth) are included as are all intermediate ranges (e.g., 0.2-0.5, 0.54-0.913, and so forth).

Example 1

Materials

Palladium (II) chloride (PdCl$_2$, ReagentPlus, 99%), potassium hexachloropalladale (IV) (K$_2$PdCl$_6$), potassium chloride (KCl), L-ascorbic acid, aluminum oxide (fused, powder, a-phase, 325 mesh), ammonium cerium nitrate (CeH$_8$N$_8$O$_{18}$) and polyvinylpyrrolidone (PVP, Mw: 40 K) were purchased from Sigma-Aldrich and used as received without further purification.

Preparation of Catalysts

Pd/α-Al$_2$O$_3$:

In a typical synthesis, K$_2$PdC$_{16}$ (0.25 mmol). PdCb (025 mmol), KCl (7.5 mmol), L-ascorbic acid (1 mmol) and PVP (10 mmol) were dissolved in 100 mL of deionized water. The mixed solution was refluxed at 100° C. for 3 h. Al$_2$O$_3$ (5 g) were added in the solution and the mixture was stirred at 60° C. until all the solvents evaporated. The product was washed with ethanol/water and ethanol for several times and vacuum dried at 60° C. overnight.

CeO$_2$/α-Al$_2$O$_3$:

Ammonium cerium nitrate (0.05 mmol) was dissolved into 10 mL of deionized water. Al$_2$O$_3$ (5 g) were added in the solution and the mixture was stirred at 60° C. until all the solvents evaporated. The mixture was dried at 100° C. overnight and then calcined at 500° C. for 5 h to get CeO$_2$/α-Al$_2$O$_3$.

Pd—CeO$_2$/α-Al$_2$O$_3$ Catalysts:

025 mmol K$_2$PdCl$_6$, 0.25 mmol PdCl$_2$, KCl (7.5 mmol), L-ascorbic acid (1 mmol), and PVP (10 mmol) were dissolved in 100 mL of deionized water, followed by refluxing at 100° C. for 3 hrs. Then CeO$_2$/α-Al$_2$O$_3$ (5 g) was added to the solution and the mixture was stirred at 60° C. until the complete evaporation of all the solvents. The resulting mixture was washed with ethanol/water and then ethanol for several times, and vacuum dried at 60° C. for 12 h.

Characterization of Catalysts

The surface areas of the catalysts were measured using nitrogen physisorption by standard Brunauer-Emmet-Teller (BET) analysis (MicromeriticsTriStar 3000 V 6.04 A). The surface areas were calculated with TriStar II 3000 software.

X-ray photoelectron spectroscopy (XPS) was measured with a Physical Electronics ESCA 5800 spectrometer which is equipped with a monochromatic Al Ka X-ray source (E=1486.6 eV). The scanning step and working pressure were 0.1 eV and 2×10$^{-9}$ mbar, respectively. Binding energies were calibrated to C1s peak at 284.5 eV.

X-ray diffraction (XRD) analyses were performed on a Rigaku Smartlab X-ray diffraction system. A Cu Kβ radiation source (λ=1.392 Å) working at 40 kV and 40 mA was used in the tests. The range of 2θ measurements was between 20° to 80° with 0.02° steps.

The morphology and the particle size as well as the dispersion of the catalysts were studied by a scanning electron microscope (SEM-EDS, FEI Quanta FEG MK2; Oxford Instruments America, Model #51-XMX0005) and a transmission electron microscopy. (TEM, FEI, Tecnai G2 F20 S-Twin 200 kV). Samples for TEM observations were prepared by dispersing the catalysts in ethanol and drying one drop of the solution on copper grids. The particle size distribution was calculated by using Image J software.

In situ diffuse reflectance infrared Fourier transform spectroscopy (DRIFTS) measurements were performed on a Nicolet iS50 FT-IR spectrometer (Thermo Scientific, Waltham, Mass., USA) equipped with a DRIFTS system with reaction chamber (Praying Mantis model, Barrick Scientific Products, Pleasantville, N.Y., USA) employing ZnSe windows. After loading 20 μL of powder samples, the cell temperature was raised to 140° C. and allowed to thermally equilibrate for ten minutes, after which the gaseous reactants were introduced at constant flow with pressure inside the reaction chamber maintained at 2 atm. The spectra are a composite of 16 scans recorded at a resolution of 4 cm$^{-1}$.

Synthesis

The measurement of catalytic activity was performed in a fix-bed continuous flow reactor. The reactor configuration is shown schematically in FIG. 1. The catalyst (3.5 g, 2 mL) was sandwiched with sands in as stainless steel tube reactor with an inner diameter of 1.2 cm. The reactant gases (18% CO, 15% $CH_3CH_2ONO$, and $N_2$ balance) were passed through the reactor at a gas hourly space velocity (GHSV) of 600-3000 h$^{-1}$. The DEO production was carried out at a temperature of 100-160° C. and under a pressure of 0.1 MPa. A thermocouple was inserted into the catalyst bed to detect the reaction temperature. Therefore, the temperature reported here is the catalyst bed temperature. A SRI 8610C gas chromatography (GC) fitted with a capillary column (Restek MXT-1 60 m×0.53 mm×5 μm) and a molecular sieves column (MS 13x) was used to analyze the tail gases. Gas chromatography/mass spectroscopy (GC-MS) for liquid products were performed with an Agilent Technology 7890A GC system with a split-splitless injector (model 7863 Auto-sampler Injector) fitted with a 5957C VLMSD MS system using a capillary column (HP-5MS, 30 m×0.250 mm×0.25 μm). When the GC analysis results show that the reaction is in steady state, the sample cylinder vessel is emptied and the start time of the reaction is recorded. Samples from the sample cylinder vessel are collected in every 6 hours and the liquid products were collected and analyzed by offline GC-MS.

Results and Discussion

Characteristics of Catalysts

Figure 2:
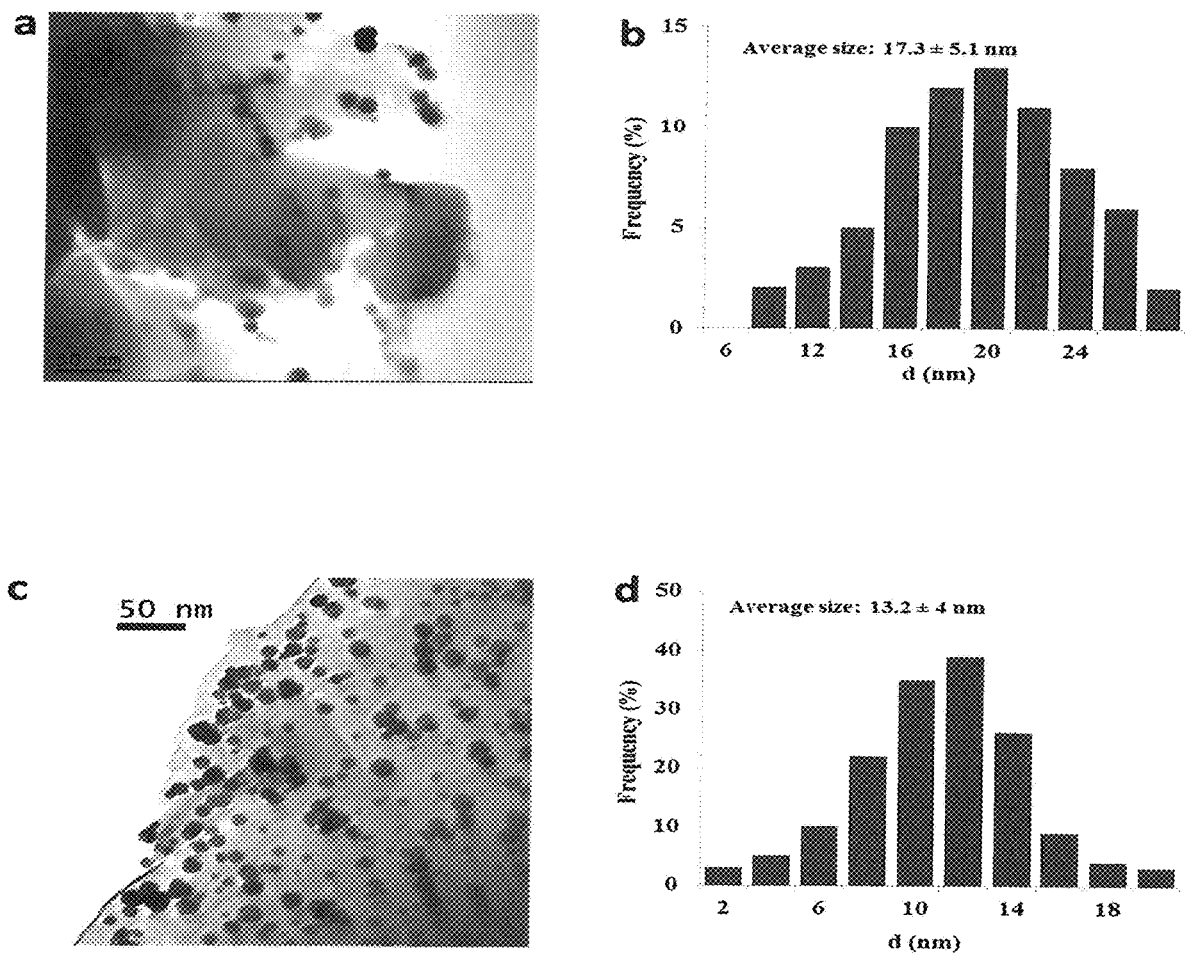
FIG. 2 shows the TEM results (a) and the size distribution of the Pd/α-Al$_2$O$_3$ catalyst (b) and the TEM results (c) and size distribution of the Pd—CeO$_2$/α-Al$_2$O$_3$ catalyst (d).

The textural characteristics of Pd—$CeO_2$/α-$Al_2O_3$ catalyst were investigated by TEM, STEM and SEM (FIG. 2). TEM images presented in FIGS. 2a and 2c clearly indicate that the Pd nanoparticles of Pd—$CeO_2$/α-$Al_2O_3$ are highly dispersed on the α-$Al_2O_3$ while the dispersion of Pd nanoparticles of Pd/α-$Al_2O_3$ is poor. Moreover, the results in FIGS. 2b and 2d show that the average Pd nanoparticles size of the Pd—$CeO_2$/α-$Al_2O_3$ catalyst is 13.2 nm which is smaller than that of the Pd/α-$Al_2O_3$ catalyst (17.3 nm). The Pd nanoparticles size distribution of the Pd—$CeO_2$/α-$Al_2O_3$ catalyst is narrower than that of the Pd/α-$Al_2O_3$ catalyst in the meanwhile. $CeO_2$ was difficult to detect by TEM maybe due to its low loading concentration. However, the red circles in Fig. S 4a indicate the dispersion of $CeO_2$ on the α-$Al_2O_3$ support, which is confirmed by energy dispersive X-ray (EDX) spectra. The dispersion of $CeO_2$ particles was not as good as Pd particles. They were aggregated into large nanoparticles with the diameters around 200 nm. In summary of the results from TEM and SEM, it can be concluded that the promoter $CeO_2$ not only promotes the dispersion of Pd on the support, but also decreases the nanoparticle size of Pd.

Figure 3:
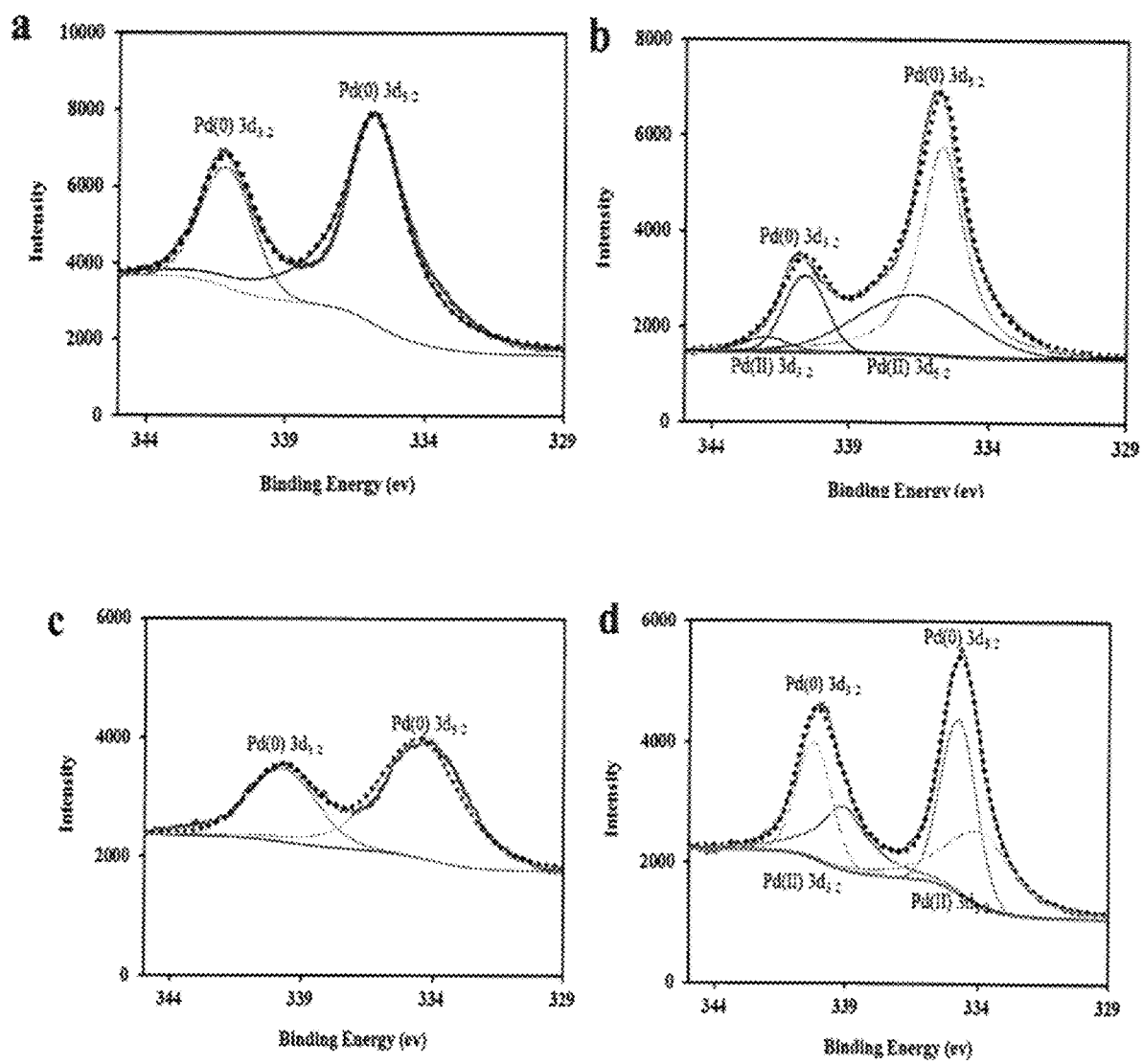
FIG. 3 shows the Pd 3d XPS spectra of catalysts Pd/α-Al$_2$O$_3$(a) before and (b) after reaction and Pd—CeO$_2$/α-Al$_2$O$_3$(c) before and (d) after reaction.

The two catalysts, Pd/α-$Al_2O_3$ and Pd—$CeO_2$/α-$Al_2O_3$, were detected with XPS (Pd 3d) before and after the reaction with CO and EN at 140° C. (FIG. 3). Although there were small differences between Pd/α-$Al_2O_3$ and Pd—$CeO_2$/α-$Al_2O_3$, the obtained Pd $3d_{3/2}$ and Pd $3d_{5/2}$ values for both Pd(0) and Pd(II) were consistent with the published literatures. [32-34] In FIGS. 3a and 3c, both the Pd $3d_{5/2}$ and Pd $3d_{3/2}$ of catalysts Pd/α-$Al_2O_3$ and Pd—$CeO_2$/α-$Al_2O_3$ are around 335 and 340 eV, respectively, which indicates that the oxidation state of Pd in the catalysts is Pd(0). However, after reaction, two new peaks appeared in both the two catalysts (FIGS. 3c and 3d), which are assigned to Pd(II), [34] indicating that some Pd(0) in the two catalysts was oxidized to Pd(II) by methyl nitrite to form an intermediate. CH30-Pd(II)-OCH3. [13] The peaks area of the Pd(II) in FIG. 3d is much bigger than the peaks area in FIG. 3b, which indicates that more intermediate were generated on the surface of Pd—$CeO_2$/α-$Al_2O_3$ catalyst, and therefore Pd—$CeO_2$/α-$Al_2O_3$ may have higher catalytic activity with the addition of $CeO_2$. Furthermore, the percentage of the Pd on both catalysts was calculated using the peaks area of the XPS, the Pd—$CeO_2$/α-$Al_2O_3$ catalyst showed higher Pd concentration (0.92%) than that of the Pd/α-$Al_2O_3$ catalyst (0.81%), which strongly suggests that the promoter $CeO_2$ can also enhance the Pd loading concentration on the support. XPS was also detected to further confirm the XPS results. However, no detectable $CeO_2$ or Pd peak was found maybe due to their low concentrations and the high dispersion of Pd.[28]

Factors Affecting the Conversion of CO/EN to DEO

Addition of $CeO_2$

Figure 4A:
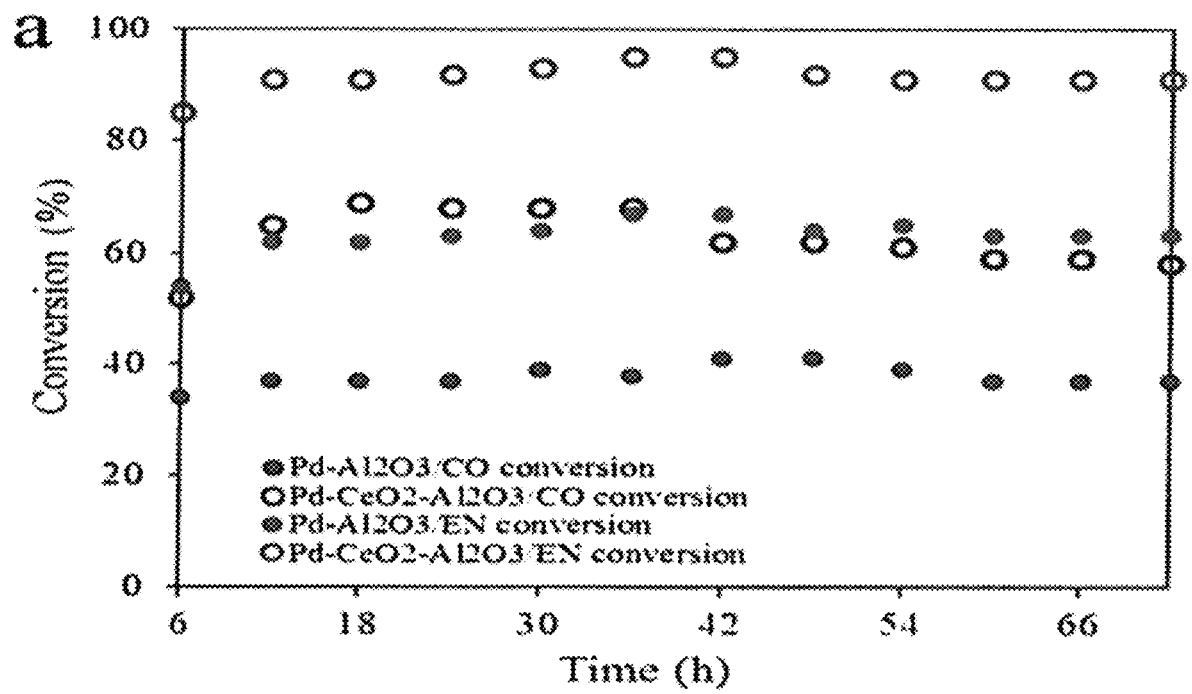
FIG. 4(a) is a chart of the conversion of CO (blue lines) and EN (red lines) of CO oxidative coupling to DEO with different catalysts within 72 h.

The catalytic performances of the two catalysts were evaluated under the same conditions. With the addition of $CeO_2$, the conversion of CO and EN was increased from 39% to 65% and 64% to 92%, respectively (FIG. 4a). There is 50% more of conversion for both of the reactants. The STY of DEO with Pd—$CeO_2$/α-$Al_2O_3$ was also greatly increased, which is 60% higher than that of Pd/α-$Al_2O_3$ at 140° C. (Table 1).

TABLE 1

CO oxidative coupling to DEO with different catalysts[a]

| Catalysts | Pd content (wt %) | Ce content (wt %) | Conversion[b] (%) | Selectivity (%) | STY (gL$^{-1}$h$^{-1}$) |
|---|---|---|---|---|---|
| Pd/α-$Al_2O_3$ | 0.8 | — | 39 | 95 | 195 |
| Pd—$CeO_2$/α-$Al_2O_3$ | 0.8 | 0.15 | 65 | 93 | 318 |
| $CeO_2$/α-$Al_2O_3$ | — | 0.2 | — | — | — |

Figure 4B:
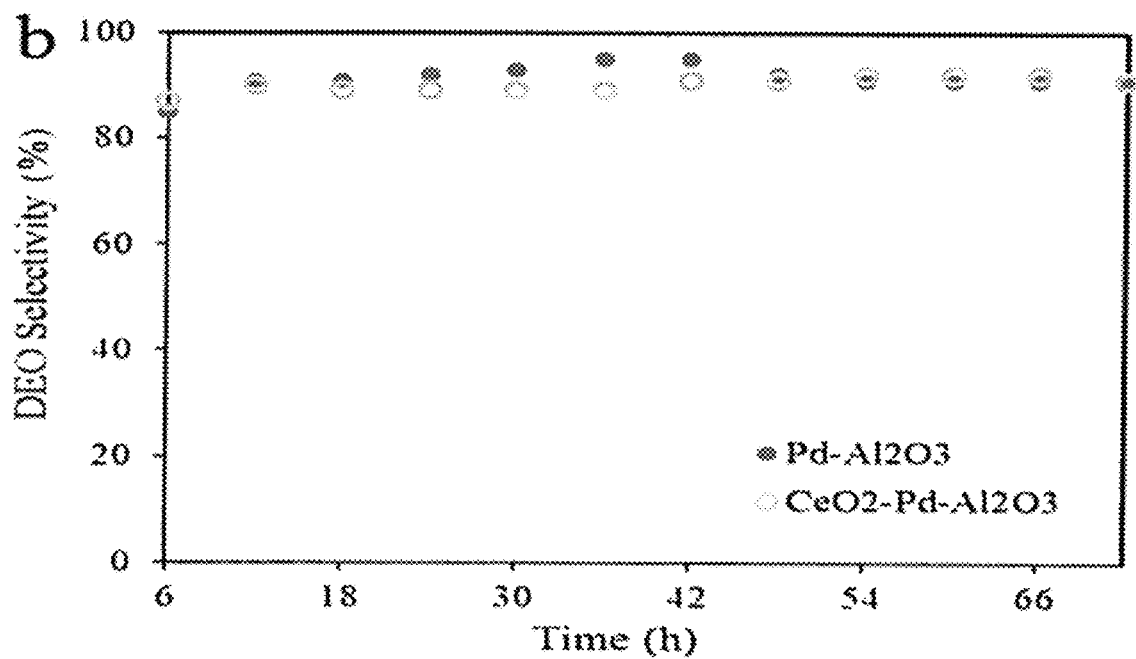
FIG. 4(b) DEO selectivity of CO oxidative coupling to DEO with different catalysts within 72 h.

[a]Reaction conditions: 3.5 g of catalyst, 1200 h$^{-1}$ of gas hourly space velocity (GHSV), reactants' volume ratio CO/EN is 1.2 0.1 Mpa, 140° C.
[b]Conversion of CO In the meanwhile, the selectivity of DEO with these two catalysts was almost the same (around 92%). Since there was no catalytic activity found for the catalyst $CeO_2$/α-$Al_2O_3$, the $CeO_2$ plays an important role as a promoter and the interaction of $CeO_2$ with Pd was responsible for the high activity and selectivity in CO oxidative coupling to DEO. Most of all, the catalytic activity of catalyst Pd—$CeO_2$/α-$Al_2O_3$ can be maintained for at least 72 h (FIG. 4b), which lays a good foundation for long-term stability.

Figure 5:
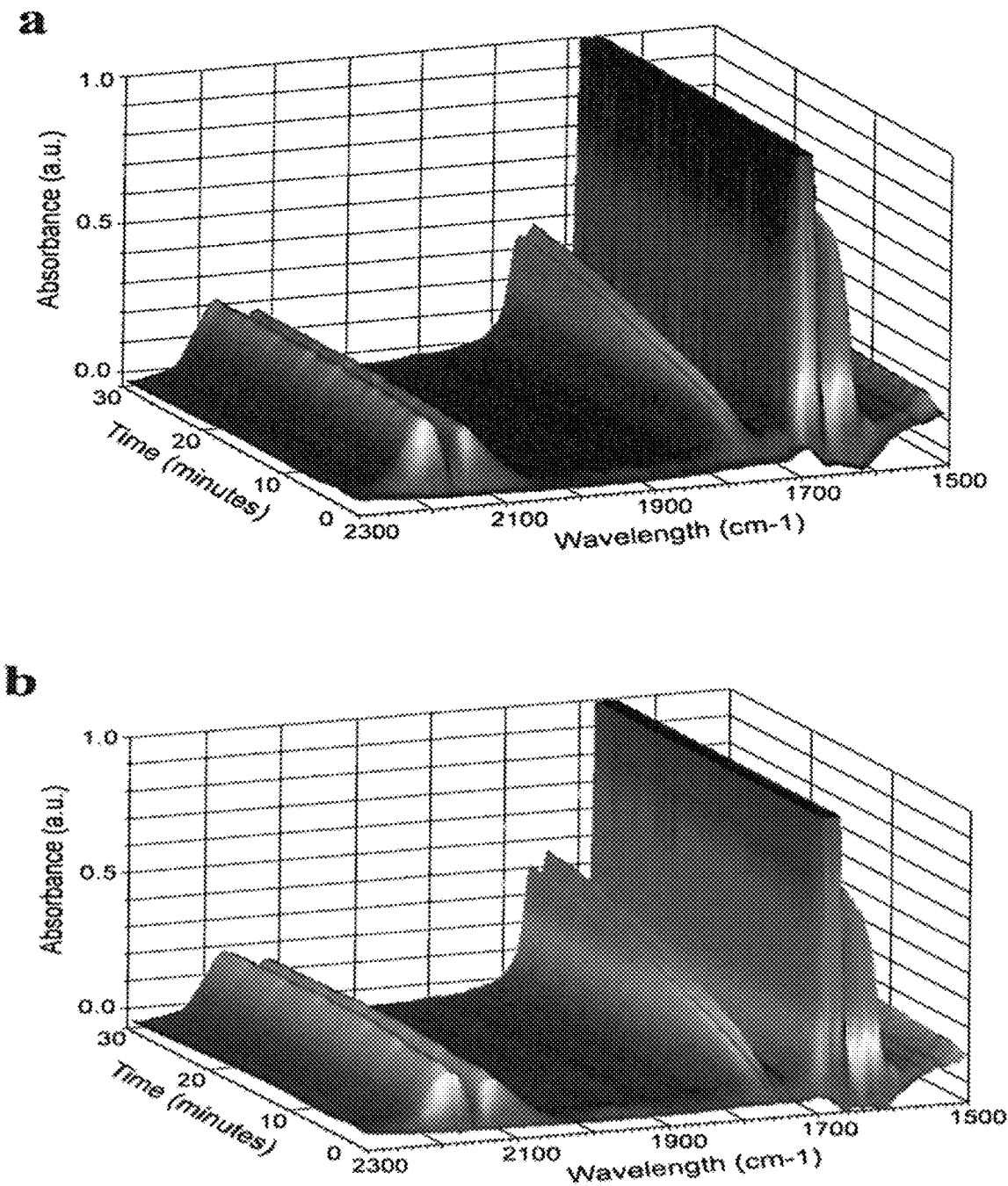
FIG. 5 are graphs of the in situ FTIR spectra for the CO oxidative coupling to DEO reaction with Pd/α-Al$_2$O$_3$(a) and Pd—CeO$_2$/α-Al$_2$O$_3$(b).

FIG. 5 illustrate the in situ DR-FTIR spectra for the reaction of CO with ethyl nitrite to DEO. The band at 1774 cm$^{-1}$ is attributed to the C═O stretching vibrations of the DEO product. It is important to note that the intensity of the band at 1774 cm$^{-1}$ in the spectrum of FIG. 5b is stronger than that in the spectrum of FIG. 5a and from the integration results of the two peaks, the peak area of Pd—$CeO_2$/α-$Al_2O_3$ catalyst is 20% bigger than that of the catalyst without $CeO_2$, which demonstrates the superior catalytic activity of Pd—$CeO_2$/α-$Al_2O_3$ relative to Pd/α-$Al_2O_3$, consistent with the results of catalytic activity evaluation and TEM, XPS results.

Temperature

Figure 6A:
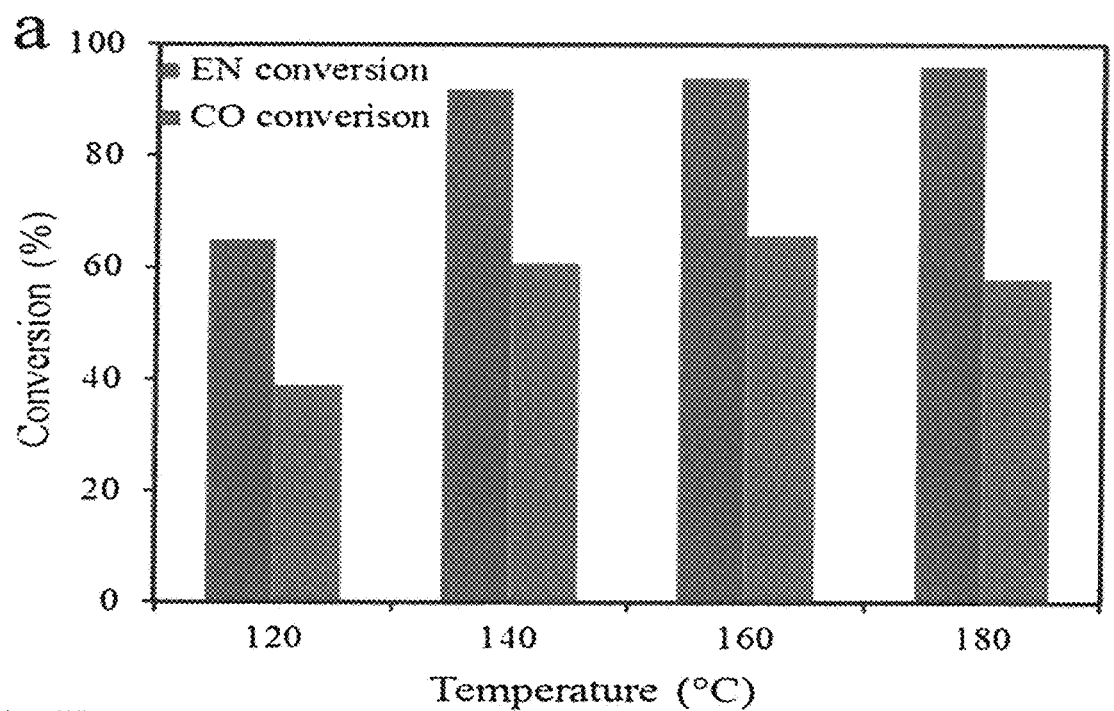
FIG. 6(a) is a graph of the conversion of CO (blue lines) and EN (red lines) of CO oxidative coupling to DEO at different reaction temperatures (reaction conditions: 3.5 g of Pd—CeO$_2$/α-Al$_2$O$_3$ catalyst, 1200 h-1 of gas hourly space velocity; reactant's volume ratio CO/EN is 1.2, 0.1 Mpa)
Figure 6B:
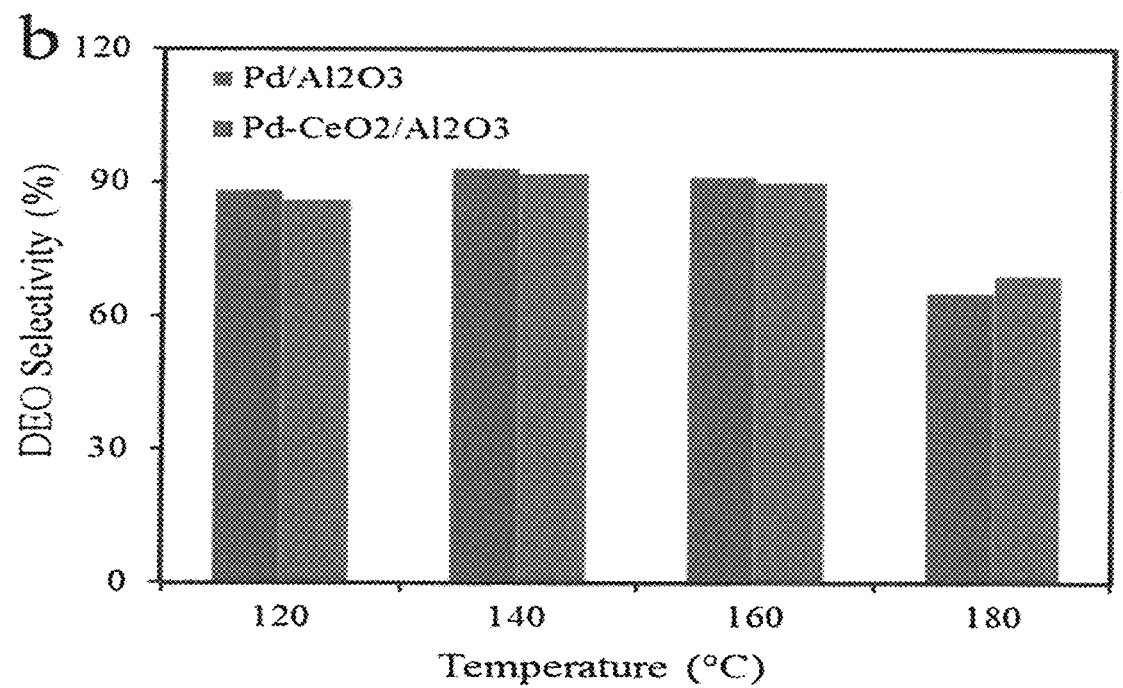
FIG. 6(b) is a chart of the DEO selectivity of CO oxidative coupling to DEO with different reaction temperatures.

FIG. 6a shows the effect of temperature on both EN and CO conversion where Pd—$CeO_2$/α-$Al_2O_3$ was used as the catalyst for CO oxidative coupling to DEO reaction. The conversion of EN and CO became higher with the temperature increasing, especially when the temperature increased from 120° C. to 140° C. Both EN and CO conversion increased 20% accordingly. However, with the temperature increasing, the selectivity of DEO had almost no change except when the temperature reached to 180° C. Both the CO conversion and DEO selectivity decreased at 180° C. due to the decomposition of the EN. The Pd—$CeO_2$/α-$Al_2O_3$ catalyst can be optimized to achieve a lower reaction temperature with high DEO selectivity.

Conclusion

In summary, a low Pd loading Pd/α-$Al_2O_3$ nanocatalyst with 0.8% Pd (wt %) loading and the average Pd size of 13.2 nm was synthesized for CO oxidative coupling to DEO. After the introduction of 0.2 wt % $CeO_2$, Pd—$CeO_2$/α-$Al_2O_3$ catalyst showed remarkably higher catalytic activity compared with the catalyst without $CeO_2$. The CO conversion was increased SO % more (from 39% to 62%) with the DEO selectivity higher than 90% when the $CeO_2$ was used as a promoter and, importantly, the high activity and selectivity could be maintained up to 72 h without visible decrease. TEM results showed clearly that $CeO_2$ not only improved the dispersion of palladium on the surface of the support but also decreased the palladium size as well, thus resulted in the excellent catalytic activity. In consideration of the facile synthesis and low Pd loading of this catalyst as well as the insecurity factors of methyl nitrite, this highly efficient and stable nanocatalyst may have a promising industrial application, especially in the US, of the coal to ethylene glycol.

The foregoing exemplary descriptions and the illustrative preferred embodiments of the present invention have been explained in the figures and tables herein and attached to this application and have been described in detail, with varying modifications and alternative embodiments being taught. While the invention has been shown, described and illustrated herein, it should be understood by those skilled in the art that equivalent changes in form and detail may be made therein without departing from the spirit and scope of the invention, and that the scope of the present invention is to be limited only as precluded by prior art. Moreover, the invention as described and disclosed herein may be suitably practiced in the absence of the specific elements which are described and disclosed herein.

REFERENCES

[1] W. Kotowski, J. Freiberg, W. Spisak, S. Zamorowskabiemacik, Przemysl Chemiczny, 68 (1989) 73-76.
[2] D. F. Othmer, M. S. Thakar, Industrial and Engineering Chemistry, 50 (1958) 1235-1244.
[3] T. J. Zhao, D. Chen, Y. C. Dai, W. K. Yuan, A. Holmen, Industrial & Engineering Chemistry Research, 43 (2004) 4595-4601.
[4] E. Jin, Y. Zhang, L. He, H. G. Harris, B. Teng, M. Fan. Applied Catalysis A: General, 476 (2014) 158-174.
[5] F. Zhang, D. Xu, Y. Wang, X. Guo, L. Xu, M. Fan, Applied Energy, 130 (2014) 1-6.
[6] S. N. Naik, V. V. Goud, P. K. Rout, A. K. Dalai, Renewable & Sustainable Energy Reviews, 14 (2010) 578-597.
[7] A. Kumar, D. D. Jones, M. A. Hanna, Energies, 2 (2009) 556-581.
[8] M. E. Dry, Abstracts of Papers of the American Chemical Society, 219 (2000) U254-U254.
[9] H. Y. Song, R. H. Jin, M. R. Kang, J. Chen. Chinese Journal of Catalysis, 34 (2013) 1035-1050.
[10] Q. L. Chen, W. M. Yang, J. W. Teng, Chinese Journal of Catalysis, 34 (2013) 217-224.
[11] J. S. Bae, L. S. Hwang, Y. J. Kweon, Y. C. Choi, S. J. Park, H. J. Kim, H. Jung, C. Han, Korean Journal of Chemical Engineering, 29 (2012) 868-875.
[12] F. X. Li, L. S. Fan, Energy & Environmental Science, 1 (2008) 248-267.
[13] Z. N. Xu, J. Sun, C. S. Lin, X. M. Jiang, Q. S. Chen, S. Y. Peng, M. S. Wang, G. C. Guo, Acs Catalysis, 3 (2013) 118-122.
[14] F. D. Meng, G. X. Xu, R. Q. Guo, H. F. Yan, M. Q. Chen, Chemical Engineering and Processing, 43 (2004) 785-790.
[15] B. Sadeghi, S. Ghamami, Chemical Engineering Communications 200 (2013) 178-184.
[16] C. W. Jiang, Z. W. Zheng, Y. P. Zhu, Z. H. Luo, Chemical Engineering Research & Design, 90 (2012) 915-925.
[17] X. C. Gao, Y. J. Zhao, S. P. Wang, Y. L. Yin, B. W. Wang, X. B. Ma, Chemical Engineering Science, 66 (2011) 3513-3522.
[18] Z. H. Gao, C. Q. Hu, Z. H. Li, F. He, G. H. Xu, Chinese Journal of Catalysis, 25 (2004) 205-209.
[19] Z. H. Gao, Q. Wu, F. He, Z. H. Li, G. H. Xu, Chinese Journal of Catalysis, 23 (2002) 95-98.
[20] Q. Wu, Z. H. Gao, F. He, Z. H. Li, G. H. Xu, Chinese Journal of Catalysis, 24 (2003) 289-293.
[21] G-H. Xu, Y. C. Li, Z. H. Li, H. J. Wang, Industrial & Engineering Chemistry Research, 34 (1995) 2371-2378.
[22] Q. Lin, X. G. Zhao, W. Bi, W. D. Xiao, Chinese Journal of Catalysis, 27 (2006) 911-915.
[23] S. Y. Peng, Z. N. Xu, Q. S. Chen, Y. M. Chen, J. Sun, Z. Q. Wang, M. S. Wang, G. C. Guo, Chemical Communications, 49 (2013) 5718-5720.
[24] X. Gao, Y. P. Zhu, Z. H. Luo, Chemical Engineering Science, 66 (2011) 6028-6038.
[25] Z. H. Gao, Z. C. Liu, F. He, G. H. Xu, Journal of Molecular Catalysis a-Chemical, 235 (2005) 143-149.
[26] Q. Lin. Y. Ji, Z. D. Jiang, W. D. Xiao, Industrial & Engineering Chemistry Research, 46 (2007) 7950-7954.
[27] Y. Yamamoto, T. Matsuzaki, S. Tanaka, K. Nishihira, K. Ohdan, A. Nakamura, Y. Okamoto, Journal of the Chemical Society-Faraday Transactions, 93 (1997) 3721-3727.
[28] X. G. Zhao, Q. Lin, W. D. Xiao, Applied Catalysis a-General, 284 (2005) 253-257.
[29] G. L. Zhuo, X. Z. Jiang, Chinese Journal of Catalysis, 24 (2003) 509-512.
[30] F. D. Meng, G. H. Xu, Q. R. Guo, Journal of Molecular Catalysis a-Chemical, 201 (2003) 283-288.
[31] Z. H. Li, Y. Song, P. Du, X. B. Ma, B. W. Wang, G. H. Xu, Reaction Kinetics and Catalysis Letters, 73 (2001) 135-142.
[32] A. Tressaud, S. K. hairoun, H. Touhara, N. Watanabe, Zeitschrift Fur Anorganische Und Allgemeine Chemie, 541 (1986) 291-299.
[33] C. J. Jenks, S. L. Chang, J. W. Anderegg, P. A. Thiel, D. W. Lynch. Physical Review B, 54 (1996) 6301-6306.
[34] W. E. Moddeman, W. C. Bowling, D. C. Carter, D. R. Grove, Surface and Interface Analysis, 11 (1988) 317-326.

We claim:

1. A highly effective catalyst for the preparation of diethyl oxalate using carbon monoxide, comprising:
an active component;
a carrier; and
a promoter agent, wherein:
the active component is palladium present in the form of particles and the particles have an average surface area within the range of 2 $m^2/g$ and 12 $m^2/g$;
the carrier is α-alumina:
the promoter agent is $CeO_2$ the loading of $CeO_2$ within 0.15 and 0.25 percent by weight; and
the catalyst demonstrates a conversion rate of at least about 62 percent.

2. The catalyst of claim 1, wherein the loading of active component is within the range of 0.1 and 1 percent by weight.

3. The catalyst of claim 2, wherein the loading of $CeO_2$ is 0.2 percent by weight.

4. The catalyst of claim 1, wherein the active component particles have an average size within the range of 2 and 80 nm and an average surface area within the range of 3 $m^2/g$ and 8 $m^2/g$.

5. The catalyst of claim 1 wherein the carbon monoxide is from coal-derived syngas.

6. A method of improving the conversion rate of carbon monoxide to diethyl oxalate by at least fifty percent by catalysts comprising:
an active component;
a carrier; and
a promoter agent,
wherein:
the active component is palladium present in the form of particles with an average surface area within the range of 3 $m^2/g$ and 8 $m^2/g$;
the carrier is α-alumina; and
the promoter agent is $CeO_2$, the loading of $CeO_2$ within 0.07 and 0.6 percent by weight.

7. The method of claim 6, wherein the active component is present at about 0.8 to 0.9 percent by weight.

8. The method of claim 7, wherein the active component particles have a size of between about 9 and 17 nm.

9. The method of claim 8, wherein the carbon monoxide is from coal derived syngas.

10. The method of claim 4, wherein the active component particles have a size of between about 9 and 17 nm.

11. The method of claim 10, wherein the active component is present between about 0.7 and 1 percent by weight.

12. The method of claim 11, wherein the active component is present at about 0.8 percent by weight and the promoter is present at about 0.2 percent by weight.

13. A method for producing diethyl oxalate comprising:
providing carbon monoxide;
providing ethyl nitrite;
providing a catalyst, the catalyst comprising:
a palladium active agent, wherein:
the palladium is present in the form of particles;
the particles have an average surface area between 2 $m^2/g$; and 12 $m^2/g$ and
the palladium loading is between 0.8 and 0.9% wt.;
a $CeO_2$ promoter, the $CeO_2$ loading being between 0.15 and 0.25% wt.; and
an α-alumina carrier; and
reacting the carbon monoxide and ethyl nitrite in the presence of the catalyst,
wherein the reaction has a carbon monoxide conversion rate greater than about 62% and an ethyl nitrite conversion rate of about 92%.

* * * * *